United States Patent
Nguyen

(10) Patent No.: US 6,844,460 B2
(45) Date of Patent: Jan. 18, 2005

(54) METHOD OF MAKING MERCAPTOALKYLALKYLDIALKOXYSILANES

(75) Inventor: Binh Thanh Nguyen, Midland, MI (US)

(73) Assignee: Dow Corning Corporation, Midland, MI (US)

(*) Notice: Subject to any disclaimer, the term of this patent is extended or adjusted under 35 U.S.C. 154(b) by 67 days.

(21) Appl. No.: 10/336,437

(22) Filed: Jan. 3, 2003

(65) Prior Publication Data

US 2004/0133025 A1 Jul. 8, 2004

(51) Int. Cl.[7] .................................................. C07F 7/04
(52) U.S. Cl. ..................................................... 556/429
(58) Field of Search .......................................... 556/429

(56) References Cited

U.S. PATENT DOCUMENTS 4,082,790 A    4/1978   Speier ..................... 260/448.8
5,223,575 A    6/1993   Mori et al. ................. 525/102

OTHER PUBLICATIONS

Preparation of Silylalkanethiols, Gornowicz et al, J. Org. Chem. 1968 33(7) pp. 2918–2924.*

* cited by examiner

Primary Examiner—Samuel Barts
(74) Attorney, Agent, or Firm—Jim L. DeCesare

(57) ABSTRACT

Mercaptoalkylalkyldialkoxysilane compositions are prepared by reacting an alkoxysilane containing an unsaturated organic group, with a sulfur containing organic acid, in the presence of a peroxide catalyst. This step produces a thiol ester. In the next step, methanolysis of the thiol ester is carried out in the presence of a basic catalyst. The resulting product is a mercaptoalkylalkyldialkoxysilane composition such as mercaptoethylmethyldimethoxysilane, mercaptomethylmethyldiethoxysilane, mercaptopropylmethyldiethoxysilane, or mercaptopropylmethyldimethoxysilane. Carrying out the first step of the reaction at least in part in the presence of air obtains maximum efficiency.

8 Claims, No Drawings

METHOD OF MAKING MERCAPTOALKYLALKYLDIALKOXYSILANES

FIELD OF THE INVENTION

One category of sealants used for industrial application are sealants cured by an oxygen induced crosslinking of certain mercaptofunctional siloxanes. Some monomers typically used in to obtain such sealants include mercaptoalkylalkyldialkoxysilanes such as the two mercaptoalkylmethyldimethoxysilanes, namely mercaptomethylmethyldimethoxysilane and mercaptoethylmethyldimethoxysilane.

This invention therefore relates to a new method of making mercaptoalkylalkyldialkoxysilanes. In particular, mercaptoethylmethyldimethoxysilane $CH_3(CH_3O)_2SiCH_2CH_2SH$ was synthesized in situ in two steps involving (i) reaction of dimethoxymethylvinylsilane $CH_3(CH_3O)_2SiCH=CH_2$ and thioacetic acid, in the presence of 2,4-dichlorobenzoyl peroxide to form a thiol ester; followed by (ii) the methanolysis of the thiol ester prepared in (i) in the presence of a basic catalyst, i.e., sodium methoxide $NaOCH_3$.

BACKGROUND OF THE INVENTION

Very few synthetic routes exist in the public domain relative to methods of making mercaptoalkylalkyldialkoxysilanes. U.S. Pat. No. 4,082,790 (Apr. 4, 1978), for example, assigned to the same assignee as the present invention, describes a process for making mercaptans similar to the compositions prepared herein, by reacting a haloalkoxysilane with a mixture containing hydrogen sulfide and either ammonia or a hydrocarbon amine such as butyl amine. However, this process suffers from the disadvantage that it requires ventilation equipment, a pressure reactor, and filtration of by-products such as ammonium chloride in an anhydrous and oxygen free atmosphere.

However, nothing in the public domain describes a method of making mercaptoalkylalkyldialkoxysilanes by reacting an alkoxysilane containing unsaturated organic groups with a sulfur containing organic acid in the presence of a peroxide catalyst, followed by methanolysis in the presence of a basic catalyst to obtain the mercaptoalkylalkyldialkoxysilane.

SUMMARY OF THE INVENTION

The invention is directed to a method of making mercaptoalkylalkyldialkoxysilane compositions in a two step reaction. The first step involves the reaction of an alkoxysilane containing an unsaturated organic group, with a sulfur containing organic acid, in the presence of a peroxide catalyst. In this first step, a thiol ester is obtained. The second step of the method is methanolysis of the thiol ester formed in the first step, in the presence of a basic catalyst. The product obtained as a result of the second step methanolysis is the desired mercaptoalkylalkyldialkoxysilane composition. Generally, the first step of the reaction should be carried out at least in part in the presence of air, to obtain maximum efficiency.

Some alkoxysilanes which can be used include diethoxymethylvinylsilane, dimethoxymethylvinylsilane, dimethoxymethylallylsilane, and diethoxymethylallylsilane. Generally, the sulfur containing organic acid is thioacetic acid or thiobenzoic acid. Preferred peroxide catalysts are 2,4-dichlorobenzyl peroxide or benzoyl peroxide. Some preferred basic catalysts include sodium methoxide, lithium methoxide, lithium ethoxide, potassium methoxide, potassium ethoxide, or sodium ethoxide.

The method is especially useful for making mercaptoalkylalkyldialkoxysilane compositions such as mercaptoethylmethyldimethoxysilane, mercaptoethylmethyldiethoxysilane, mercaptopropylmethyldimethoxysilane, and mercaptopropylmethyldiethoxysilane.

These and other features of the invention will become apparent from a consideration of the detailed description.

DETAILED DESCRIPTION OF THE INVENTION

Mercaptoalkylalkyldialkoxysilanes which can be prepared according to the invention generally conform to the formula $R(OR)_2SiR'SH$ in which R is an alkyl group containing 1–6 carbon atoms such as methyl, ethyl, propyl, isopropyl, and butyl, or a cycloalkyl group such as cyclopentyl and cyclohexyl; and R' is a divalent alkylene linking group with 2–6 carbon atoms such as ethylene, 1,2-propylene, 2-methyl-1,3-propylene, and 3-methyl-1,3-propylene.

Some specific examples of the mercaptoalkylalkyldialkoxysilanes which can be prepared according to the invention include, for example, mercaptoethylmethyldimethoxysilane $CH_3(CH_3O)_2SiCH_2CH_2SH$, mercaptoethylmethyldiethoxysilane $CH_3(C_2H_5O)_2Si\,CH_2CH_2SH$, mercaptopropylmethyldimethoxysilane $CH_3(CH_3O)_2SiCH_2CH_2CH_2SH$, and mercaptopropylmethyldiethoxysilane $CH_3(C_2H_5O)_2SiCH_2CH_2CH_2SH$.

Some examples of alkoxysilanes containing unsaturated organic groups include, for example, diethoxymethylvinylsilane $CH_3(C_2H_5O)_2SiCH=CH_2$, dimethoxymethylvinylsilane $CH_3(CH_3O)_2SiCH=CH_2$, dimethoxymethylallylsilane $CH_3(CH_3O)_2SiCH_2CH=CH_2$, and and diethoxymethylallylsilane $CH_3(C_2H_5O)_2SiCH_2CH=CH_2$.

The sulfur containing organic acid can be, for example, thioacetic acid $CH_3COSH$ or thiobenzoic acid $C_6H_5COSH$. Peroxide catalysts which can be used include, for example, 2,4-dichlorobenzyl peroxide or benzoyl peroxide. Some examples of useful basic catalysts are sodium methoxide $NaOCH_3$, lithium methoxide $LiOCH_3$, lithium ethoxide $LiOC_2H_5$, and sodium ethoxide $NaOC_2H_5$, potassium methoxide $KOCH_3$, and potassium ethoxide $KOC_2H_5$.

According to the method of the invention, and to explain the method in more detail, mercaptoethylmethyldimethoxysilane $CH_3(CH_3O)_2SiCH_2CH_2SH$ was synthesized in situ in two steps by (i) the addition of thioacetic acid to dimethoxymethylvinylsilane $CH_3(CH_3O)_2SiCH=CH_2$ in the presence of a silicone oil containing 50 percent by weight of 2,4-dichlorobenzoyl peroxide, to form an intermediate thiol ester, followed by (ii) the methanolysis of the intermediate thiol ester, in the presence of the basic catalyst sodium methoxide ($NaOCH_3$), to form the desired mercaptoalkylalkyldialkoxysilane.

This two step reaction is shown below in a simplified equation in which Me is used to represent the methyl group and Vi is used to represent the vinyl group.

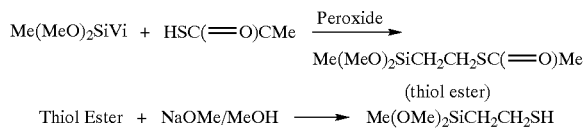

It was found that the most efficient reaction of thioacetic acid with $Me(MeO)_2SiVi$ in the presence of a peroxide catalyst such as 2,4-dichlorobenzoyl peroxide, can be obtained when it is air assisted. It appears that air has a beneficial effect on forming the thiol ester. The most effective process can be carried out by sparging air into the reaction mixture. This feature is shown in the two Examples 1 and 2 shown below.

Methanolysis typically requires a basic catalyst. An excess of methanol is generally used, as its presence in excess insures completion of the reaction. Methanol can be removed by distillation. The pH during this procedure should be maintained at between about 10 to about 12. Any remaining excesses of basic catalysts such as sodium methoxide can be removed by gravity filtration.

The relative amounts of the reactants and other components used in the both steps of the process can be varied. It is preferred to carry out the process under stoichiometric conditions, and a stoichiometric excess is typically only required in the case of methanol, for reasons noted above. The process can be carried out batch-wise or continuously, but batch processing is the most preferred mode. While contact between the reactants can occur at temperatures between −80 to 350° C., preferably the temperature is maintained between about 50 to about 150° C., most preferably between 70–100° C. The optimum reaction time is variable depending upon the reactants, the reaction temperature, and the concentration of the various reactants and components. Ordinarily, there is no benefit in extending the contact time of the reactants and components beyond 24 hours, but likewise there is usually no harm, unless extremely low temperatures are employed. With most of the particular reactants and components used herein, practical quantitative yields can be obtained in 12 hours. The reaction can be carried out at atmospheric, sub-atmospheric, or super-atmospheric pressure. Here again, the choice of conditions is largely a matter of logic, based upon the nature of the reactants, and the equipment available. Non-volatile reactants are especially adaptable to being heated at atmospheric pressure with or without a reflux arrangement. Reactants which are gaseous at ordinary temperatures are preferably reacted at substantially constant volume under autogenous or induced pressure. The best results are obtained by maintaining all reactants and components used in the process in the liquid phase.

The following examples are set forth in order to illustrate the invention in more detail. In the examples, gas chromatography (GC) data were obtained on a Hewlett Packard Model 5890 GC device equipped with a Chromosorb W HP 80 mesh column operated isothermally at 160° C. using a flame ionization detector (FID). A Hewlett Packard Model 3392A recording integrator was used for quantification. Gas Chromatography/Mass Spectrometry (GC/MS) was also obtained from Hewlett Packard's Model 5890 GC equipped with Model 5970 Series Selective Detector. A Perkin Elmer 1600 Series Fourier Transform Infrared (FTIR) Spectroscopy device was used to obtain infrared spectra.

EXAMPLE 1

Synthesis of Mercaptoethylmethyldimethoxysilane—Argon/Air Assisted

Methyldimethoxyvinylsilane (500 g, 3.78 mol) and 7 g of a peroxide catalyst in the form of a solution containing 50 percent by weight of 2,4-dichlorobenzoyl peroxide dispersed in a silicone oil, were loaded into a 2 liter 3-neck round bottom flask equipped with a magnetic bar and stirrer, an addition funnel, a 30' Allihn reflux condenser, an argon inlet system, a heating mantle, and a thermometer and thermocouple connected to a Gardsman temperature control unit. The peroxide catalyst was a product of Elf Atochem North America Inc., Philadelphia, Pa., sold under the trademark Luperco® CST. The mixture in the flask was heated to 85–90° C. under an argon atmosphere. A slightly yellow mixture was observed. An excess of thioacetic acid (322 g, 4.24 mol) was added to the hot mixture via an additional funnel at a rate of 5 mL/min. The addition of the acid was completed in less than one hour, and a dark orange mixture was seen. GC analysis of the mixture showed only 0.65 percent of the thiol ester $CH_3(CH_3O)_2SiCH_2CH_2SC(=O)CH_3$. The reaction temperature was maintained at 85–90° C. After four hours, GC analysis of the mixture showed 2.6 percent of the thiol ester. At this time, the argon inlet system was discontinued. The reaction mixture as then sparged with air. After 5 minutes, GC analysis of the mixture showed 15.5 percent of the thiol ester. After 7 hours of air sparging, a dark brown reaction mixture was observed, and GC analysis of the mixture indicated the presence of only trace amounts of unreacted methyldimethoxyvinylsilane. At this point, a solution containing 87.5 g of sodium methoxide in 788 g of methanol was added slowly to the mixture. The pH of the resulting mixture was between 10–12. Periodic addition of sodium methoxide was required to maintain the pH above 10. The reaction temperature was maintained at 80–85° C. After 5 hours, GC analysis of the mixture indicated the presence of less than one percent of the unreacted thiol ester. The mixture was then distilled to remove any low boiling materials such as methanol, dimethyl carbonate, and any unreacted low boiling point compounds that may have been present. The residue was heated to distill mercaptoethylmethyldimcthoxysilane at atmospheric pressure. However, when the temperature reached 150–160° C., the mixture solidified. As a result, the mixture was cooled and distilled under reduced pressure to recover the product at 36–40° C./18 mm Hg. Collected was 80 g of mercaptoethylmethyldimethoxysilane with a purity of 80 percent.

EXAMPLE 2

Conducted Under Air Atmosphere Following by Air Sparging

This example was carried out under an air atmosphere. Methyldimethoxyvinylsilane (200 g, 1.51 mol) and 3 g of the peroxide catalyst used in Example 1, were loaded into the same equipment used in Example 1. The mixture was heated to 85–90° C. A slightly yellow mixture was observed. An excess of thioacetic acid (161 g, 2.12 mol) was added to the hot mixture via an additional funnel at a rate of 5 mL/min. The addition was completed within 30 minutes and a dark orange mixture was observed. GC analysis of the mixture 15 minutes after completion of the addition of the thioacetic acid showed 10 percent of the thiol ester $CH_3(CH_3O)_2SiCH_2CH_2SC(=O)CH_3$. At this point, air was sparged into the mixture, and stirring of the mixture was continued at 85° C. After 5 hours, a dark brown reaction mixture was observed. GC analysis of the mixture showed that the conversion of methyldimethoxysilane to the thiol ester was nearly completed. At this time, 57 g of a solution containing 25 percent by weight of sodium methoxide in 173 ml of methanol was added slowly to the mixture. The pH of the resulting mixture was 11–12.Periodic addition of sodium methoxide was necessary to maintain the pH above 10. The reaction temperature was maintained at 80–85° C. After 6 hours, GC analysis of the mixture showed the presence of one percent of any of the unreacted thiol ester. The mixture was cooled to room temperature, filtered to remove excess sodium methoxide, and then distilled to remove excess methanol, dimethyl carbonate, and any unreacted low boiling point materials. The residue was then fractionally distilled on a 24/40 joint J-Head with a 20 cm Vigreaux column under reduced pressure. The distillation yielded (i) 45 g of mercaptoethylmethyldimethoxysilane with a purity of 87 percent at 85° C./40 mmHg; (ii) 31.5 g of mercaptoethylmethyldimethoxysilane with a purity of 91 percent at 86° C./40 mmHg; and (iii) 70 g of mercaptoethylmethyldimethoxysilane with a purity of 96 percent at 88–89° C./40 mmHg. The overall yield of this in situ two step synthesis of mercaptoethymethyldimethoxysilane was 75 percent. Infrared (IR) spectra showed a moderate stretching absorption band at 2565 cm$^{-1}$ which is characteristic of the S-H band.

Table 1 shows some properties of mercaptoalkylalkyldialkoxysilanes which can be prepared according to the method of the present invention. Me in the table represents methyl.

TABLE 1

Physical Properties Of Mercaptoalkylalkyldialkoxysilanes

| Compound(s) | M.W. | B.P. (° C./mmHg) | Density (g/cc) |
|---|---|---|---|
| Me(MeO)$_2$SiCH$_2$SH | 152 | 69–70/50 | 1.027 |
| Me(MeO)$_2$SiCH$_2$CH$_2$SH | 166 | 88–89/40 | 1.008 |
| Me(MeO)$_2$SiCH$_2$CH$_2$CH$_2$SH | 180 | 96/30 | 1.000 |

Other variations may be made in compounds, compositions, and methods described herein without departing from the essential features of the invention. The embodiments of the invention specifically illustrated herein are exemplary only and not intended as limitations on their scope except as defined in the appended claims.

What is claimed is:

1. A method of making a mercaptoalkylalkyldialkoxysilane composition comprising first (i) reacting an alkoxysilane selected from the group consisting of, diethoxymethylvinylsilane, dimethoxymethylvinylsilane, dimethoxymethylallylsilane, and diethoxymethylallylsilane with a sulfur containing organic acid, in the presence of a peroxide catalyst, to obtain a thiol ester; followed by the (ii) methanolysis of the thiol ester formed in (i), in the presence of a basic catalyst, to obtain the mercaptoalkylalkyldialkoxysilane composition.

2. The method according to claim 1 in which the sulfur containing organic acid is thioacetic acid or thiobenzoic acid.

3. The method according to claim 1 in which the peroxide catalyst is 2,4-dichlorobenzyl peroxide or benzoyl peroxide.

4. The method according to claim 1 in which the basic catalyst is sodium methoxide, lithium methoxide, lithium ethoxide, potassium methoxide, potassium ethoxide, or sodium ethoxide.

5. The method according to claim 1 in which the mercaptoalkylalkyldialkoxysilane composition is mercaptoethylmethyldimethoxysilane, mercaptomethylmethyldiethoxysilane, mercaptopropylmethyldimethoxysilane, or mercaptopropylmethyldimethoxysilane.

6. The method according to claim 1 in which the first step (i) of reacting an alkoxysilane containing an unsaturated organic group, with a sulfur containing organic acid in the presence of a peroxide catalyst, is carried out at least in part in the presence of air.

7. A method of making a mercaptoalkylalkyldialkoxysilane composition comprising first (i) reacting an alkyldialkoxysilane containing an unsaturated organic group, with a sulfur containing organic acid, in the presence of a peroxide catalyst, to obtain a thiol ester; followed by the (ii) methanolysis of the thiol ester formed in (i), in the presence of a basic catalyst, to obtain the mercaptoalkylalkyldialkoxysilane composition.

8. The method according to claim 7 in which the alkyldialkoxysilane containing an unsaturated organic group is one of diethoxymethylvinylsilane, dimethoxymethylvinylsilane, dimethoxymethylallylsilane, and diethoxmethylallylsilane.

* * * * *

UNITED STATES PATENT AND TRADEMARK OFFICE
CERTIFICATE OF CORRECTION

PATENT NO. : 6,844,460 B2
DATED : January 18, 2005
INVENTOR(S) : Binh Thanh Nguyen It is certified that error appears in the above-identified patent and that said Letters Patent is hereby corrected as shown below:

Title page,
Item [57], ABSTRACT,
Line 9, the term "mercaptomethylmethyldiethoxysilane," should be changed to
-- mercaptoethylmethyldiethoxysilane --.

Column 1,
Lines 11-13, the phrase "mercaptomethylmethyldimethoxysilane and mercaptoethylmethyldimethoxysilane" should be changed to
-- mercaptoethylmethyldimethoxysilane and mercaptoethylmethyldiethoxysilane --.

Column 6,
Line 15, the term "mercaptomethylmethyldiethoxysilane," should be changed to
-- mercaptoethylmethyldiethoxysilane --.

Signed and Sealed this

Twenty-fifth Day of October, 2005

JON W. DUDAS
*Director of the United States Patent and Trademark Office*